(12) United States Patent
Hoover et al.

(10) Patent No.: US 8,310,368 B2
(45) Date of Patent: Nov. 13, 2012

(54) WEIGHT CONTROL DEVICE USING BITES DETECTION

(75) Inventors: Adam Hoover, Clemson, SC (US); Eric Muth, Clemson, SC (US); Yujie Dong, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 381 days.

(21) Appl. No.: 12/686,656

(22) Filed: Jan. 13, 2010

(65) Prior Publication Data
US 2010/0194573 A1    Aug. 5, 2010

Related U.S. Application Data

(62) Division of application No. 09/436,323, filed on Nov. 8, 1999, now Pat. No. 6,602,469.

(60) Provisional application No. 61/144,203, filed on Jan. 13, 2009, provisional application No. 60/107,707, filed on Nov. 9, 1998, provisional application No. 60/144,705, filed on Jul. 20, 1999.

(51) Int. Cl.
*G08B 23/00* (2006.01)

(52) U.S. Cl. ....... 340/573.1; 340/573.7; 368/9; 368/109

(58) Field of Classification Search ............... 340/573.1, 340/573.7; 368/9, 109; 600/503
See application file for complete search history.

(56) References Cited

U.S. PATENT DOCUMENTS

| | | | |
|---|---|---|---|
| 4,207,673 A | 6/1980 | DiGirolamo et al. | |
| 4,321,674 A | 3/1982 | Krames et al. | |
| 4,575,804 A | 3/1986 | Ratcliff | |
| 4,686,624 A | 8/1987 | Blum et al. | |
| 4,823,808 A | 4/1989 | Clegg et al. | |
| 4,911,256 A | 3/1990 | Attikiouzel | |
| 4,914,819 A | 4/1990 | Ash | |
| 4,975,682 A | 12/1990 | Kerr et al. | |
| 5,398,688 A | 3/1995 | Laniado | |
| 5,421,089 A * | 6/1995 | Dubus et al. | 30/142 |
| 5,548,283 A * | 8/1996 | Martin | 340/870.01 |
| 5,563,850 A * | 10/1996 | Hanapole | 368/89 |
| 5,864,518 A | 1/1999 | Geiser | |
| 5,908,301 A * | 6/1999 | Lutz | 434/236 |

(Continued)

FOREIGN PATENT DOCUMENTS
WO     WO 9728738 A1    8/1997

OTHER PUBLICATIONS

Amft et al., "Detection of eating and drinking arm gestures using inertial body-worn sensors," *Proceedings of the 2005 Ninth IEEE International Symposium on Wearable Computers*, 4 pages.

(Continued)

*Primary Examiner* — Hoi Lau
(74) *Attorney, Agent, or Firm* — Dority & Manning, P.A.

(57) ABSTRACT

The present invention relates to a device that can be used in individual weight control protocols that is capable of detecting in real time information with regard to number of bites taken, time between bites, and so forth. The weight control device can detect bites through motion detection via a sensor worn on the wrist or hand of a user. The device can include notification capabilities that can alert a user as to excessive eating speed, excessive amounts of food intake, and the like so as to provide immediate feedback for purposes of weight control.

36 Claims, 9 Drawing Sheets

U.S. PATENT DOCUMENTS

| | | | |
|---|---|---|---|
| 6,135,950 A | 10/2000 | Adams | |
| 6,473,368 B1 | 10/2002 | Stanfield | |
| 6,508,762 B2 | 1/2003 | Karnieli | |
| 6,735,477 B2 | 5/2004 | Levine | |
| 2002/0109600 A1* | 8/2002 | Mault et al. | 340/573.1 |
| 2002/0126014 A1* | 9/2002 | Nishitani et al. | 340/573.1 |
| 2002/0167863 A1 | 11/2002 | Davis et al. | |
| 2004/0176666 A1 | 9/2004 | Chait | |
| 2005/0245793 A1 | 11/2005 | Hilton et al. | |
| 2006/0064037 A1 | 3/2006 | Shalon et al. | |
| 2006/0197670 A1* | 9/2006 | Breibart | 340/573.1 |
| 2008/0036737 A1 | 2/2008 | Hernandez-Rebollar | |
| 2008/0137486 A1* | 6/2008 | Czarenk et al. | 368/9 |

OTHER PUBLICATIONS

Amft et al., "Methods for Detection and Classification of Normal Swallowing from Muscle Activation and Sound," *PHC 2006: Proceedings of the First International Conference on Pervasive Computing Technologies for Healthcare*, 10 pages.

Ballerini et al., "Testing MRI and Image Analysis Techniques for Fat Quantification in Meat Science," *2000 IEEE Nuclear Science Symposium*, vol. 3, pp. 18-136-18-140—Conference Record.

Blaskó et al., "Exploring Interaction with a Simulated Wrist-Worn Projection Display," *Proceedings of the 2005 Ninth IEEE International Symposium on Wearable Computers*, 8 pages.

Chambers et al., "Hierarchical Recognition of Intentional Human Gestures for Sports Video Annotation," *Pattern Recognition 2002: Proceedings. 16th International Conference*, vol. 2, 2002, pp. 1082-1085.

Ching et al., *Fitness Monitor System*, IEEE TENCON 2003, Conference on Convergent Technologies for the Asia-Pacific Region, Poster Papers, vol. 4, pp. 1399-1403.

Gagnadre et al., "Fibre optic sensor for physiological parameters," *Electronics Letters*, vol. 34, No. 21, 15th Oct. 1998, pp. 1991-1993.

Guthausen et al., "Measurement of Fat Content of Food with Single-Sided NMR," *JAOCS*, vol. 81, No. 8, Aug. 2004, pp. 727-731.

Harland et al., "High resolution ambulatory electrocardiographic monitoring using wrist-mounted electric potential sensors," *Institute of Physics Publishing, Measurement Science and Technology*, vol. 14, No. 7, Jul. 2003, pp. 923-928.

Heil et al., "Characterizing free-living light exposure using a wrist-worn light monitor," *Applied Ergonomics*, vol. 33, No. 4, 2002, pp. 357-363.

Howard et al., "Lightglove Wrist-Worn Virtual Typing and Pointing," *Proceedings of the 5th IEEE International Symposium on Wearable Computers*, 2001, pp. 172-173.

Junker et al., "Gesture spotting with body-worn inertial sensors to detect user activities," *Pattern Recognition 41*, 2008, pp. 2010-2024.

Kandaswamy et al., "Chemometric Modeling of Fat, Cholesterol and Caloric Content of Fresh and Cooked Ground Beef with NIR Reflectance Spectroscopy," *The Instrumentation, Systems and Automation Society*, Sicon/05—Sensors for Industry Conference, Feb. 8-10, 2005, pp. 52-58.

Lementec et al., "Recognition of Arm Gestures Using Multiple Orientation Sensors: Gesture Classification," *2004 IEEE Intelligent Transportation Systems Conference*, Washington, D.C., Oct. 3-6, 2004, pp. 965-970.

Limdi et al, "Design of a Microcontroller-based Device for Deglutition Detection and Biofeedback," *IEEE Engineering in Medicine & Biology Society 11th Annual International Conference*, 1989, pp. 1393-1394.

Maurer et al., "eWatch: A Wearable Sensor and Notification Platform," *Proceedings of the International Workshop on Wearable and Implantable Body Sensor Networks*, 2006, 4 pages.

Orgris et al., "Using Ultrasonic Hand Tracking to Augment Motion Analysis Based Recognition of Manipulative Gestures," *Proceedings of the Ninth IEEE Symposium on Wearable Computers*, 2005, pp. 152-159.

Ouchi et al., "LifeMinder: A Wearable Healthcare Support System with Timely Instruction Based on the User's Context," *IEICE Transactions on Information and Systems*, vol. E87-D, No. 6, 2004 IEEE, pp. 445-450.

Ouchi et al., "LifeMinder: A Wearable Healthcare Support System Using User's Context," *Proceedings of the 22nd International Conference on Distributed Computing Systems Workshops*, 2002, 2 pages.

Saeki et al., "Proposal of Food Intake Measuring System in Medical Use and Its Discussion of Practical Capability," *Knowledge-Based Intelligent Information and Engineering Systems*, 9th International Conference, KES 2005, Proceedings, Part III (Lecture Notes in Artificial Intelligence, vol. 3683, pp. 1266-1273.

Schmidt et al., "Learning an Orchestra Conductor's Technique Using a Wearable Sensor Platform," *Proceedings of the 2007 11th IEEE International Symposium on Wearable Computers*, 2007, 2 pages.

Sharples et al. "A technical review of mobile computational devices," *Journal of Computer Assisted Learning*, vol. 19, No. 3, Sep. 2003, pp. 392-395.

Smailagic et al., "eWatch: Context Sensitive System Design Case Study," *Proceedings of the IEEE Computer Society Annual Symposium on VLSI*, 2005 IEEE, 6 pages.

Sugimoto et al., "Development of a wrist-worn calorie monitoring system using bluetooth," *Microsyst Technol.*, vol. 11, No. 8-10, Aug. 2005, pp. 1028-1033.

Takeda et al., "Dish Extraction Method with Neural Network for Food Intake Measuring System on Medical Use," *CIMSA 2003—International Symposium on Computational Intelligence for Measurement Systems and Applications*, Jul. 29-31, 2003, pp. 56-59.

Villanueva et al., "Spatial Resolution of a Noninvasive Measurement of the Arterial and Venous Input Function Using a Wrist Monitor," *2003 IEEE Nuclear Science Symposium Conference Record—Nuclear Science Symposium, Medical Imaging Conference*, V. 4, 2003, pp. 2232-2236.

Wong et al., "Portable Accelerometer Device for Measuring Human Energy Expenditure," *IEEE Transactions on Biomedical Engineering*, vol. BME-28, No. 6, Jun. 1981, pp. 467-471.

Yao et al., "A Video Processing Approach to the Study of Obesity," *2007 IEEE International Conference*, Jul. 2-5, 2007, pp. 1727-1730.

Zhu et al., "Technology-Assisted Dietary Assessment," *Proc. of SPIE-IS&T Electronic Imaging*, SPIE vol. 6814, 2008, 681411-11681411-10.

Product Information on LIS3L02AL—MEMS Inertial Sensor: 3-axis—+/−2g ultracompact linear accelerometer from ST, May 2006, 10 pages.

Product Manual for use with InertiaCube3 and the InertiaCube3 Processor from Intersense, 2005, 13 pages.

Zhang, et al., "Detection of Activities by Wireless Sensors for Daily Life Surveillance: Eating and Drinking", Sensors, 2009, 9, pp. 1499-1517.

Article—Bushnell, "The Don't-Diet Way to Lose Weight" *SELF*, Apr. 1987, pp. 150-153.

Article—Mahoney, "The Obese Eating Style: Bites, Beliefs and Behavior Modification", *Addicitive Behaviors*, vol. 1, pp. 47-53 (1975).

Search Report and Written Opinion for PCT/US2010/020873 dated Mar. 22, 2010, 9 pages.

* cited by examiner

WEIGHT CONTROL DEVICE USING BITES DETECTION

CROSS REFERENCE TO RELATED APPLICATION

This application claims filing benefit of U.S. Provisional Patent Application Ser. No. 61/144,203 having a filing date of Jan. 13, 2009, which is incorporated herein by reference in its entirety.

BACKGROUND

According to the Center for Disease Control (CDC), in the years 2005 and 2006, more than one third of American adults were obese. In addition, the percentage of Americans that are overweight continues to increase. Eating disorders that can lead to individuals being extremely over or underweight have been connected to a myriad of health problems including hypertension, osteoarthritis, dysiipidemia, type 2 diabetes, coronary heart disease, stroke, gallbladder disease, sleep apnea, respiratory problems, cancers (i.e. endometrial, breast, colon, etc.), and reproductive complications.

Society as a whole also pays a price for increasing levels of obesity. For instance, in the year 2000 the estimated national cost due to obesity was 117 billion dollars. An estimated 61 billion dollars was attributed to direct costs such as preventive, diagnostic, and treatment services. In addition, an estimated 56 billion dollars was accredited to indirect costs such as value of income lost from decreased productivity, restricted activity and value of future income lost due to premature death.

Obviously, there is a need to provide individuals with additional and improved methods and devices to obtain and maintain a healthy weight. Many methods and devices have been developed over the years to promote healthy eating habits. For instance, a plurality of devices have been developed that utilize a database capable of storing information, e.g., caloric information, fat/protein/carbohydrate breakdown, etc., for a large number of food items. Such devices can be used to monitor the amount of food and calorie intake that one consumes during a given day. Examples of such devices are described in U.S. Pat. Nos. 4,321,674 to Krames et al., 4,686,624 to Blum et al., 4,575,804 to Ratcliff, 4,911,256 to Attikiouzel, and PCT Patent Application No. WO 97/28738 to Zuabe. Unfortunately, such devices lack the ability to provide real time feedback to a user. Also, many of these devices require the user to enter information into a computer which takes time and effort. Most such devices are not applicable for general, everyday-use for food intake monitoring. It is a tedious effort to manually track or note in a diary every meal consumed, and manual tracking provides obvious opportunities for bias and misreporting. Moreover, devices developed for clinical or hospital or research monitoring of food intake are not applicable for everyday use by an average person.

Devices that offer real time feedback to a user have also been described. For instance, U.S. Pat. No. 5,398,688 to Laniado describes a device that can detect changes in physiological variables such as heart rate, stroke volume, and blood pressure corresponding to initiation of eating. A detected change in a physiological variable starts a timer and after a predetermined amount of time has passed the device will notify the user to stop eating.

U.S. Pat. No. 5,563,850 to Hanapole describes a device that alerts the user when it is acceptable to take another bite based upon the time interval between individual bites. The device utilizes a wrist motion detector that activates a timer upon wrist motion.

U.S. Pat. No. 6,135,950 to Adams describes a device that includes a first sensor placed on a user's throat to monitor swallowing and a second sensor that is placed near the user's heart. Feedback from the two sensors allows better quantification of the amount of food ingested.

Other sensors have been developed to monitor other bodily functions. For instance, U.S. Patent Application Publication No. 2005/0245793 to Hilton, et al. describes an apparatus and methodology that may be used to measure and store physiological parameters indicative of sustained activity by a user including walking, sleeping, exercising, or other activities.

While the above describe improvements in the art, room for additional improvement exists. What is needed in the art is a noninvasive, inexpensive, easy to operate, discreet device that can measure food intake. For instance, a device that can be worn casually, and can provide a system such that feedback and recording capabilities do not embarrass the user would be of great benefit.

SUMMARY

According to one embodiment, disclosed is a device for determining that a bite of food has been taken by a subject. For instance, a device can include a sensor that monitors motion of the hand, arm, wrist, or any combination thereof of a subject, e.g., a multi-axis accelerometer. In one preferred embodiment, a device can include a sensor that monitors positive and negative roll motion of the hand, arm, wrist, or any combination thereof of a subject. A device can also include an electronic processor for receiving raw data from the sensor and carrying out data manipulation to form processed data. The processed data can include information concerning the recognition of a single bite as well as the number of bites of food taken by the subject. A device can also include an electronic memory for storing the processed data, a user interface for providing to the subject information concerning the bite recognition, e.g., the number of bites of food taken by the subject over a period of time or during a meal, and an attachment device for attaching the sensor to the clothing or body of the subject, e.g., a wrist band.

A device can include additional sensors as well. By way of example, sensors to monitor the pitch and/or yaw motion of the hand, arm, and/or wrist of the subject, to monitor a physiological property of the subject, to monitor the time between individual bites, and the like.

In one embodiment, a device can include a housing that encloses, e.g., the sensor, the electronic processor, and/or the electronic memory. Moreover, a memory can store information concerning only a single or multiple meals. For instance, in one embodiment, a memory can store information concerning the number of bites taken during a meal, during a day, during a week, etc., and can compile and provide that information over a long term, such as over several months. Thus, a user can be provided with long term records of the number of bites taken and can correlate that information with a targeted desired weight.

A device can also include a power source, a communications link for transferring data from the device to an external device, or any other desirable features.

Also disclosed is a method for determining that a bite of food has been taken by a subject. For example, a method can include sensing raw data concerning positive and negative roll motion of the hand, arm, wrist, or any combination thereof of a subject and electronically processing the raw data with a processor to develop processed data. The processed data can comprise a pattern of motion, the pattern of motion including (a) a positive roll of the hand, arm, wrist, or any combination thereof of a subject, (b) a negative roll of the hand, arm, wrist, or any combination thereof of a subject; and (c) a pause in roll motion between the positive roll and the negative roll motions, wherein upon recognition of the pattern of motion, the processor determines that a bite of food has been taken by the subject. A pause length can be preset depending upon an individual's eating methods or an average pause length, such as between about 0.5 and about 10 seconds, or between about 1 and about 7 seconds, or between about 1 and about 4 seconds, for instance about 2 seconds. A method can also include electronically storing the processed data in a memory, and providing information concerning the processed data to the subject via a user interface according to, e.g., auditory, tactile, and/or visual signals.

According to one preferred embodiment, the positive roll of the hand, arm and/or wrist of the subject is determined when a positive roll velocity exceeds a threshold positive roll velocity and the negative roll of the hand, arm, and/or wrist of the subject is determined when a negative roll velocity exceeds a threshold negative roll velocity. For instance, the threshold positive roll velocity can be between about +5 degrees per second and about +15 degrees per second and the threshold negative roll velocity can be between about −5 degrees per second and about −15 degrees per second.

Processing of the data can include any or all of solving any bound problems in the raw data, smoothing the raw data, and determining the derivative of the smoothed data.

BRIEF DESCRIPTION OF THE FIGURES

A full and enabling disclosure of the present subject matter, including the best mode thereof, to one of ordinary skill in the art, is set forth more particularly in the remainder of the specification, including reference to the accompanying figures, in which.

Figure 1:
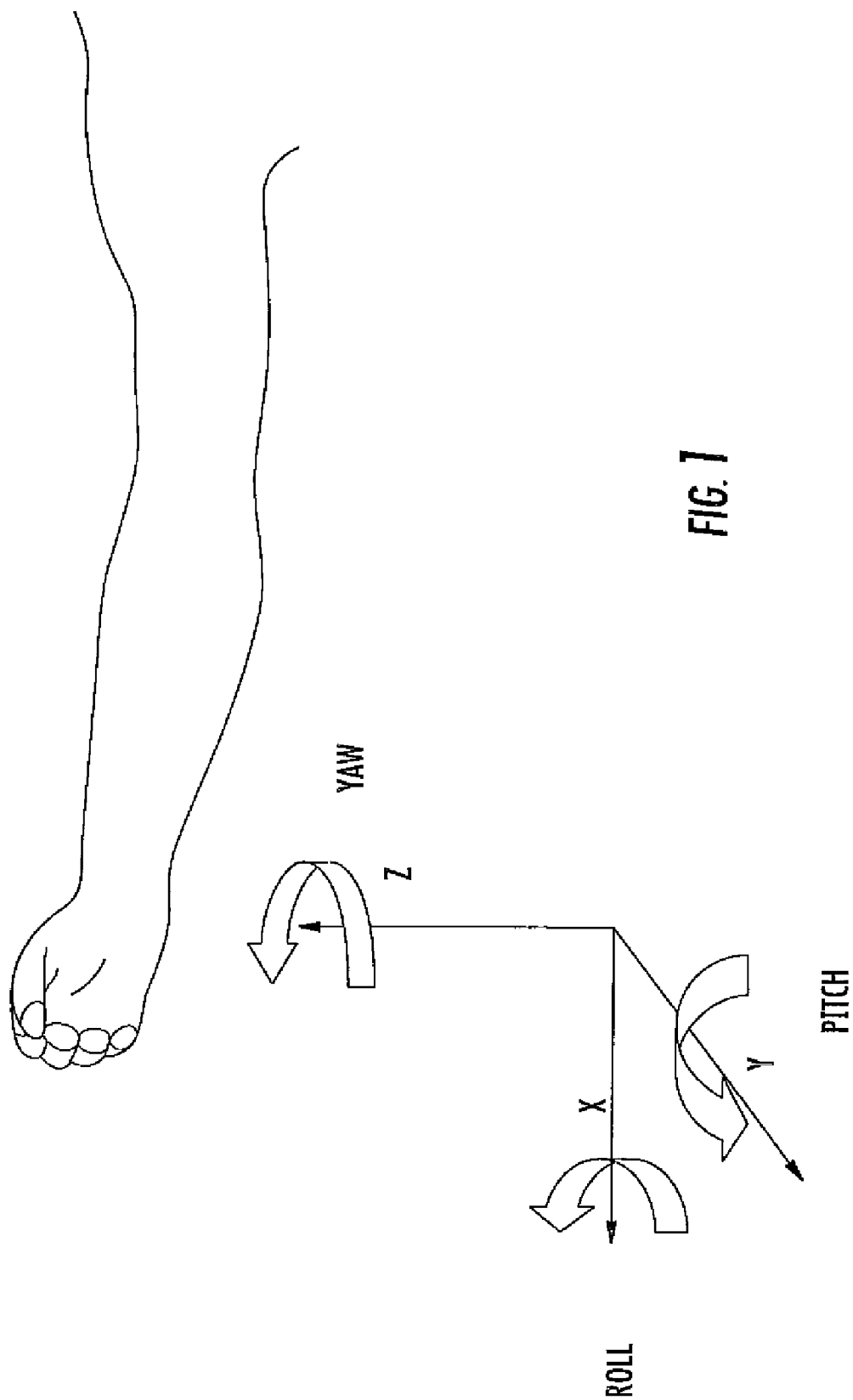
FIG. 1 is a schematic illustrating the terms pitch, yaw, and roll with reference to a human arm and as utilized herein.

Repeat use of reference characters in the present specification and drawings is intended to represent the same or analogous features or elements of the presently disclosed subject matter.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made to the disclosed subject matter without departing from the scope or spirit of the disclosure. For instance, features illustrated or described as part of one embodiment may be used with another embodiment to yield a still further embodiment.

In general, the present disclosure is directed to a device capable of aiding a user in weight control. More specifically, a device as disclosed herein is capable of detecting in real time information with regard to bites taken during a meal. For instance, a device can detect that a bite has been taken; the total number of bites taken during a meal, a day, or over another defined period of time; time between each bite; and the like. During use, disclosed devices can gather and interpret information with regard to motion of a user's wrist, arm, or hand during a meal, with particular emphasis given in one embodiment to the rolling motion of the user's wrist, hand, or arm. Of course, when referring herein to the motion of a user's hand, arm, or wrist, the present disclosure is intending to refer to the hand, arm, or wrist that is being used in carrying the utensil or the food to the subject's mouth. Information gathered can be utilized to provide real time feed back to a user, for instance a warning that a user is eating too fast or has eaten too much food or not enough food. Information can also be stored to maintain a long term record of eating, so as to better examine a user's eating habits over time.

In an exemplary configuration, a weight control device has been developed as a small electronic device that may be configured to be worn by an individual and to monitor hand, arm, and/or wrist motion of the wearer during a meal. Measurements obtained may be stored in an onboard memory device for later retrieval. For example, a weight control device in accordance with the present technology may correspond to a wristband mounted device physically resembling a watch although other wear options are envisioned.

One positive aspect of a device in accordance with the present technology is that a user may comfortably wear the device for extended periods. The ability to comfortably wear the device for extended periods can provide not only ease of use but additional motivation to continue use of the device to provide the long term feedback and data necessary to effectively monitor an extended program as may be preferred to ensure long-term change of eating habits.

Another positive aspect of a device in accordance with the present technology is that a user can be provided data over very long term periods. For instance, a user can be provided data with regard to the number of bites taken during meals over the course of several months, and that information can be utilized to provide clear, objective information to a user so as to correlate a targeted weight with a user's eating habits. For example, a long-term data log can be utilized to illustrate to a subject that a change in weight can be correlated to the number of bites of food taken by the user during each day.

In accordance with one aspect of an embodiment of the present subject matter, methodologies have been developed to provide visual indications based on real time analysis of data collected from wrist roll motion of a user. Visual indications may be employed to assist the user in acknowledging when an appropriate amount of food has been ingested during a single meal.

In accordance with additional aspects of an embodiment of the present subject matter, apparatus and accompanying methodologies have been developed to collect and evaluate long term data, for instance over the course of several months, to track the user's progress toward prescribed or target goals relating to his or her own target weight.

Figure 2:
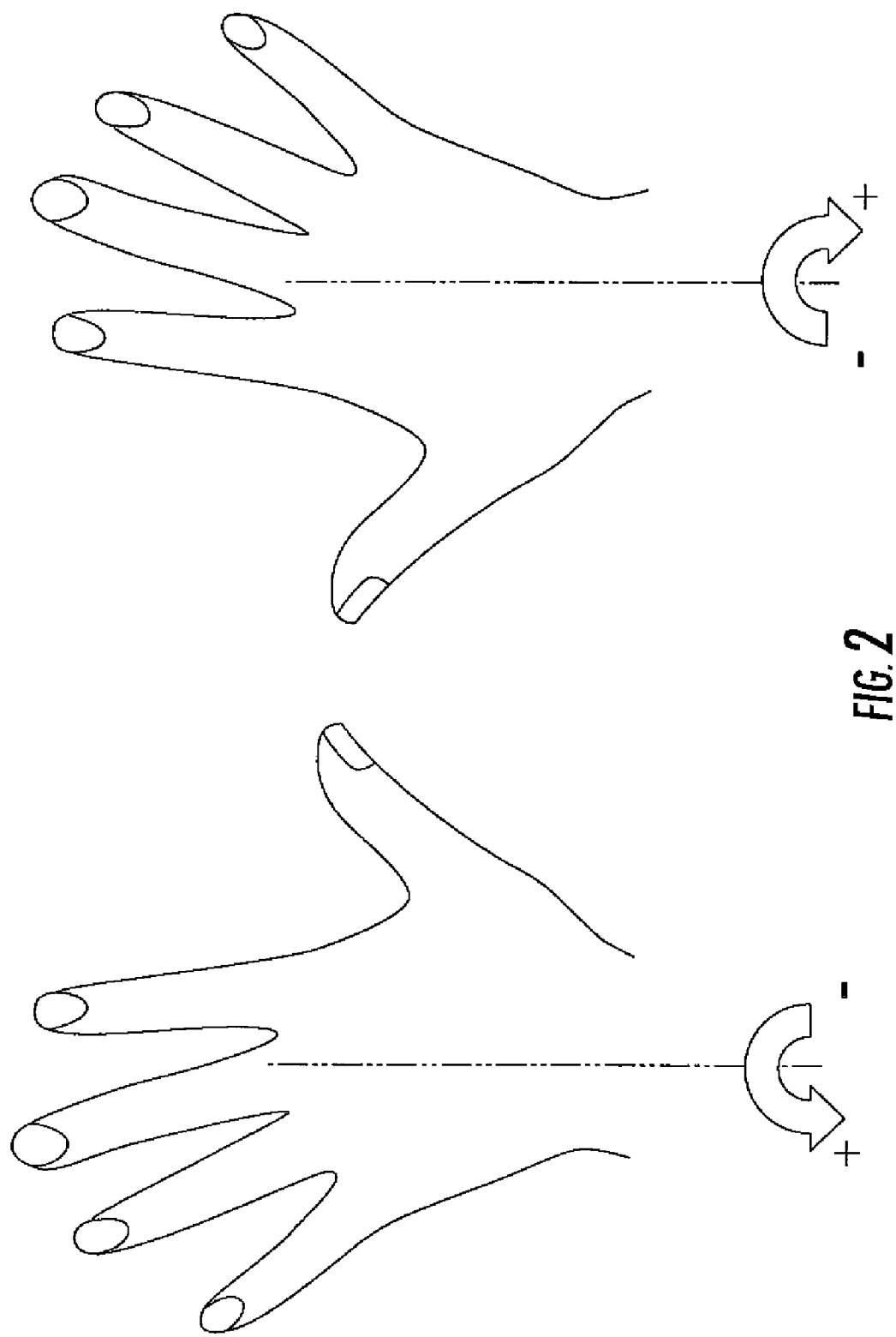
FIG. 2 is a schematic illustrating negative and positive roll as the terms are utilized herein.

Referring now to the drawings, FIGS. 1 and 2 illustrate the directional terms utilized throughout this disclosure. As can be seen in FIG. 1, and with reference to a human arm, the terms roll, pitch, and yaw as utilized herein correspond to rotation about the x, y, and z-axis, respectively, with the x-axis corresponding to the axial length of the arm, as illustrated. FIG. 2 illustrates a right and left hand, positive roll being defined as illustrated by the direction of the arrows and the + signs in FIG. 2 as the direction of supination, i.e., a clockwise roll for the right hand and a counterclockwise roll for the left hand. Negative roll as utilized herein generally refers to the direction of pronation, i.e., a counterclockwise roll for the right hand and a clockwise roll for the left hand, as illustrated in FIG. 2 by the − sign.

Devices and methods disclosed herein are based upon the realization that during the course of eating, the lower arm and hand, and primarily the wrist, undergoes a characteristic series of motions that is indicative of a single bite. Specifically, a bite can be broken down into three separate components, the first being the lifting of the food to the mouth, the second being the time during which the food is placed into the mouth, and the third being the return of the hand to the food source, e.g., the plate. The present devices beneficially take advantage of the realization that during the first and third components of a bite, the lower arm undergoes a characteristic motion, for instance with regard to roll motion. According to one embodiment, during the first recognized component of the bite, the lower arm will undergo a positive roll, this motion will be followed by a pause, and during the third recognized component, the lower arm will undergo a negative roll. Thus, the combination of the three components, positive roll, pause, negative roll, can provide a recognizable motion cycle by which a single bite can be differentiated from other motion of the arm.

Figure 3:
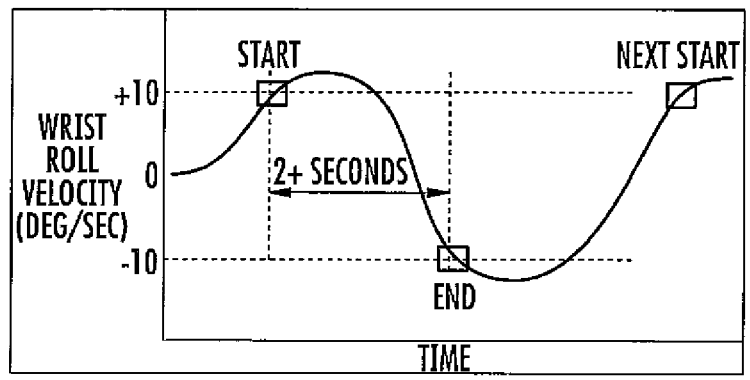
FIG. 3 graphically illustrates the characteristic roll motions associated with the taking of a single bite.

FIG. 3 graphically illustrates this characteristic series of motions for a wrist during the taking of a single bite as measured by wrist roll velocity in degrees per second. As can be seen, when the velocity of wrist roll is measured over time, the three characteristic events can be tracked to define the overall motion that corresponds to a bite. During the initial stage, the wrist roll velocity surpasses a predetermined positive threshold (+10 degrees/second in this exemplary embodiment). During the second stage, a predetermined period of time can elapse that accounts for the time to place the food into the mouth (set as 2 seconds in this exemplary embodiment). During the third and final stage, the wrist roll velocity surpasses a predetermined negative threshold (−10 degrees/second in this exemplary embodiment). The detection of these three events in sequence provides evidence that a person has taken a bite of food. Specific parameters for a detection regime can vary depending upon individual characteristics of a user, application environments (e.g., type and style of meal), and the like, as discussed further within.

It should be understood that the wrist roll can be measured according to other parameters, in addition to or alternative to velocity as mentioned above. For instance, devices as disclosed herein can measure wrist, hand or arm roll and can do so through measurement of raw orientation with no timing aspect involved. In general, however, a timing aspect can be utilized in combination with the measurement of change in orientation, irrespective of the method of sensing, so as to improve capability of differentiation of individual bites taken during a meal from other types of motion that can occur involving wrist or arm roll.

The characteristic series of bite components can be used to differentiate wrist or arm motions due to non-eating activities, such as moving food around a plate or engaging in other activities, from motions that can be directly associated with taking a bite of food. Beneficially, the detection of this characteristic series including positive and negative wrist roll separated by a pause is indifferent to the time taken between bites. Accordingly, disclosed devices can function as a direct bite detector, rather than utilizing timing, heart rate, sounds, etc, to indirectly estimate the number of bites taken during a meal.

Figure 4:
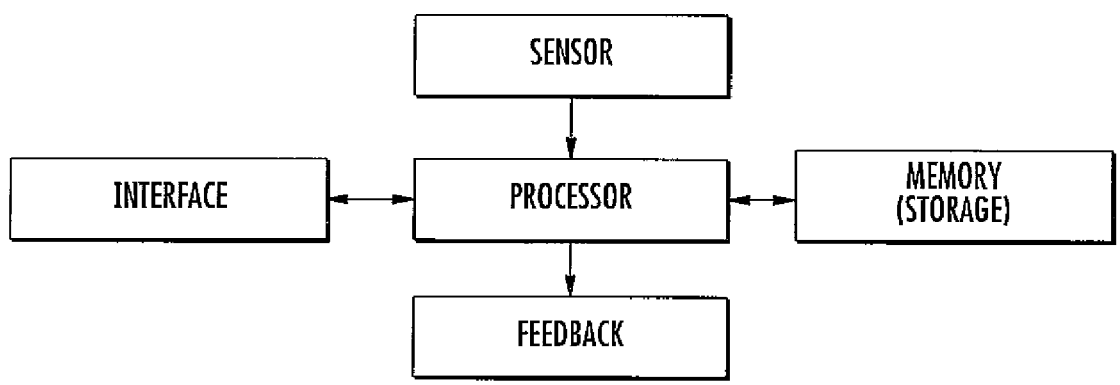
FIG. 4 provides a system diagram of one embodiment of a device as disclosed herein.

According to the disclosed subject matter, devices can be provided that advantageously incorporate the capability to detect and communicate information regarding the characteristic series of motions indicative of the taking of a single bite during a meal. For example, FIG. 4 provides a system diagram of a device according to one representative embodiment. According to this embodiment, a system can include a sensor, a processor, a memory, an interface, and a feedback mechanism.

Figure 5A:
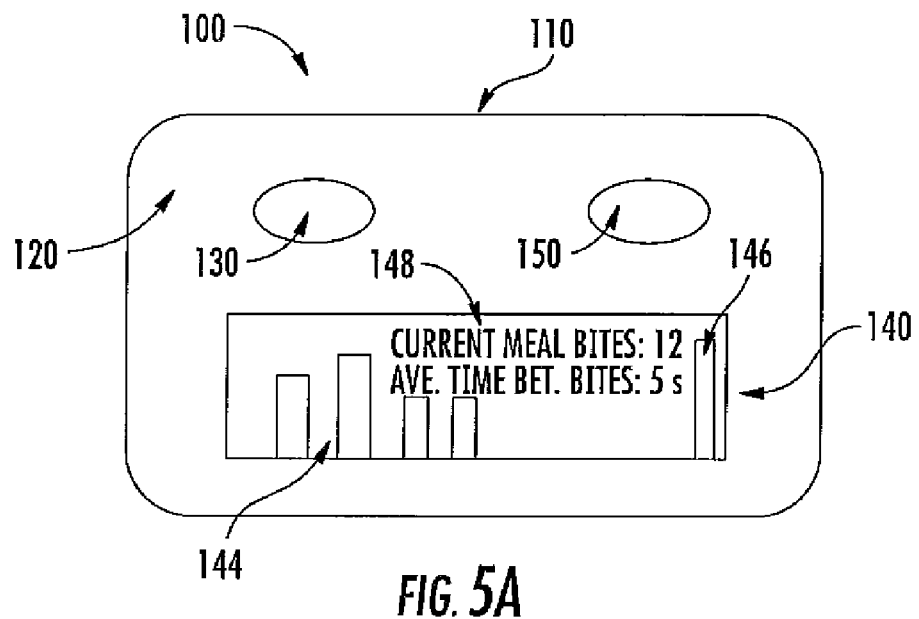
FIGS. 5A-5C schematically illustrate one embodiment of a device as described herein.
Figure 5B:
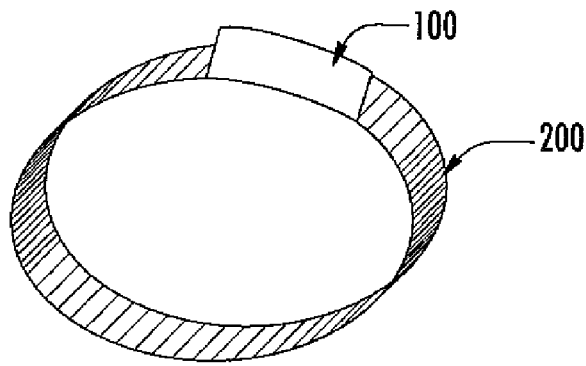
Figure 5C:
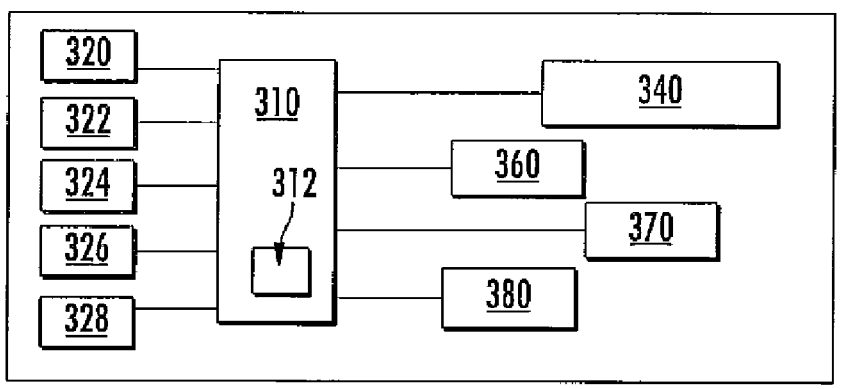

FIG. 5 illustrates an exemplary physical configuration of a device 100 in accordance with the present technology embodying a system as illustrated in FIG. 4. As may be seen from FIGS. 5A-5C, a device 100 may be configured as a small electronic device that may be attached to the arm, wrist or hand of an individual user. In an exemplary embodiment, device 100 may be attached to an adjustable wristband 200 as illustrated in FIG. 5B, however such user attachment method is not a specific limitation of the present technology, it only being required that the device 100 be associated with the user in a manner permitting detection of hand, arm and/or wrist motion.

In exemplary embodiments of the present technology, a device 100 may be attached to the arm, wrist or hand of an individual user by way of any expandable bracelet or cuff or any other suitable means. For instance, wristband 200 can be attached to a user's wrist according to any device or method including, without limitation, a hook and eye closure (e.g., Velcro®), or a buckle. In addition, wristband 200 may include one or more materials in any suitable combination including metal, plastic, woven and/or nonwoven textiles, and the like. It should be noted that any method for attaching a device 100 to the wrist, arm, or hand of a user is encompassed by the present disclosure. For instance, device 100 may include clips, loops, or so forth so as to be attachable to a user's clothing or body. In one embodiment, device 100 may include an adhesive surface, and may be adhered directly to a user's skin.

In general, device 100 may be relatively small, for instance less than about 3 cm by about 3 cm by about 1 cm, so as to be inconspicuously carried by a user and so as to avoid impedance of a user's motion. Device 100 may completely enclose the components contained therein, or may partially enclose the components contained therein. For example, device 100 may include an access port (not shown) that may provide access to the interior of device 100. In one embodiment, an access port may be covered with a removable cover, as is known in the art.

A device 100 may be paired with other objects that can be worn on the wrist or arm. For instance, a device 100 can be combined on a wrist band with a watch or decorative items or designs such that the device 100 is not overly apparent to other persons who are in the vicinity of the user.

With further reference to FIG. 5A, it will be seen that device 100 is provided with a housing 110 enclosing a number of electronic components as will be more fully described later with reference to FIG. 5C. As illustrated in FIG. 5A, device 100 is provided with a front panel 120 on which can be control and display elements to provide a user with operational control of the device 100 as well as feedback of data and other information as may be useful to the user. Principal components mounted on the front panel 120 to the device 100 include an on/off switch 130, a display panel 140 and a visual indicator 150, each of which will be more fully described herein.

With further reference to FIG. 5A, display panel 140 is configured to provide visual indications of properties monitored by device 100. Thus in an exemplary embodiment, display panel 140 may correspond to a liquid crystal display (LCD) and light emitting diode (LED) display combination or other suitable display device and may display information in the form of operational bar graph or other graphical information 144, battery charge level 146, and meal information 148, in the illustrated example, number of bites for the current meal (12) and average time between bites for the current meal (5 seconds). Graphical information of display 144 can include, for example, an historical record of total bites taken during previous meals. These displays may optionally be provided as color displays where variations in color may be associated with different visual cues for the user.

Device 100 can incorporate an on/off switch 130 that allows a user to turn the device on at the beginning of each meal and a visual indicator 150 that can allow a user to see that the device is working properly.

With reference now to FIG. 5C, there is illustrated an exemplary configuration of operational components of an exemplary device 100 in accordance with the present technology. The electronic circuit required to provide operational enablement of a device 100 may, in an exemplary embodiment, correspond to a processor 310, associated sensors 320, 322, 324, 326, 328, display device 340 and other elements as will be described later.

A processor 310 can be a microcontroller, microprocessor, system on chip (SOC), or any processor capable of being incorporated in a device 100. A processor 310 can incorporate therein an internal clock capable of measuring time. In general, a processor 310 can receive data from sensors 320, 322, 324, 326, 328, and can carry out desired data manipulation according to input instruction. For example, processor 310 can store information about detected bites in a memory 312, and retrieve this information for further computations at a later time. Memory can be integral to the processor (for example in the case of an SOC) or separable there from (for example a memory chip). Moreover, a device 100 can utilize multiple different memory devices and methods, as are known in the art.

Processor 310 can interact with a user interface that performs device-level operations. These operations could include, for example, turning the device on and/or off, resetting bite counts or other internally stored data, downloading internally stored data to an external computer, setting the time and date, and setting the parameters of the methods used to detect bites. Options can control how the feedback is provided to the user. Other operations can customize the operation of the device based upon the user's preferences. For example, the device can be made to operate only in certain time-of-day windows, or to provide certain types of feedback only when specific bite counts have been reached over a give period of time or over a single meal.

Processor 310 may correspond to a microcontroller depending on the desired operational capabilities of the device 100. For example, if a relatively simple construction or model of device 100 is desired, e.g., one capable of limited operation, a microcontroller may be used. A more functionally advanced model of device 100 may require more sophisticated onboard processing capability and, thus, may require the use of a microprocessor.

With further reference to FIG. 5C, operational circuitry of device 100 may include a number of sensors 320, 322, 324, configured to be responsive to changes in roll, pitch and yaw, respectively. For instance, a detector 100 can sense motion of a user's wrist, arm, or hand. Motion sensing can include vertical and/or horizontal motion, motion in yaw, pitch, and roll orientation or in any combination of possible motion types in order to recognize and detect an individual bite. In one preferred embodiment, sensors can detect changes in at least the roll orientation of the user's wrist, arm and hand, though information from the other orientations can also be detected, in conjunction with recognition in change in roll orientation.

Figure 6:
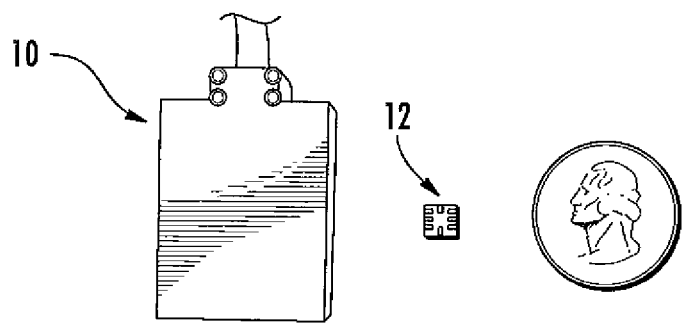
FIG. 6 illustrates two exemplary sensors as may be utilized in forming a device as disclosed herein.

Any sensor type may be utilized including, without limitation, a gyroscope, a magnetometer, a multi-axis accelerometer, or a magnetic angular rate and gravity (MARG) sensor. In one embodiment, a single sensor may be utilized that may correspond to a multi-axis accelerometer whose outputs may be used to calculate relative motion of the user's wrist in order to differentiate between individual bites during a meal. Such sensors can sense angular rate of rotation, gravity, and earth magnetic field along all three perpendicular axes, these angular rates are then integrated to obtain the orientation change (yaw, pitch and roll) of the sensor. Exemplary sensors as may be utilized in a device can include, without limitation, an inertial sensor, such as the InertiaCube 3 sensor produced by InterSense Corporation (Bedford, Mass.), which is available in wireless or wired form, as well as smaller devices, including micro-electromechanical systems (MEMS) inertial sensors such as those produced by STMicroelectronics Corporation (Geneva, Switzerland). FIG. 6 illustrates an InertiaCube 3 sensor 10 and an MEMS sensor 12. Both wireless and wired InterSense sensors are the same size, the pictured sensor 10 using a wire to connect to a computer. The STMicroelectronics sensor 12 is much smaller and produces a somewhat noiser measurement.

A device can contain additional sensors such as a gravitometer 326 and a compass 328 that can provide additional orientation or other information to a user. Additional sensors can, for example, prevent the accumulation of gyroscopic drift.

In one embodiment, device 100 can be calibrated at the start of each meal. For example, a device can be programmed to operate for a short time to record resting orientations of the device for an individual user and/or to establish a motion threshold. For instance, a device 100 can operate for a period of time from about 1 second to about 30 seconds, from about 5 seconds to about 15 seconds, or for about 10 seconds in a calibration mode. During this time, resting orientations can be recorded and a motion threshold can be established that can be utilized to better categorize motion during eating as either biting motion or non-biting motion.

Figure 7:
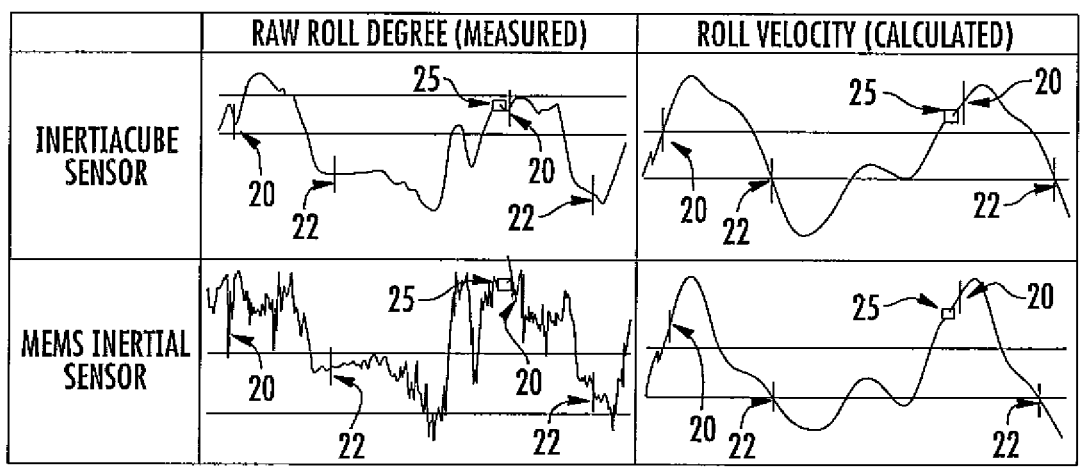
FIG. 7 illustrates data recorded simultaneously by two devices each including one of the sensors of FIG. 6.

A sensor can detect motion of a wearer and feed data to a processor that can be programmed to interpret the data and differentiate individual bites. For example, FIG. 7 illustrates raw roll degree (measured) obtained from an InertiaCube sensor 10 and a MEMS inertia sensor 12 as illustrated in FIG. 6 that were worn by a single individual at the same time, and thus recorded the same motion. As can be seen, the raw data contains an amount of noise. Accordingly, in certain embodiments, it may be preferred to further manipulate the raw data, for instance within an on-board processor 310 to provide more consistent output from a device. For example, the sensors 10, 12 illustrated in FIG. 6 measure raw orientation. In order to provide the data as roll velocity (velocity of the change in orientation), the following algorithm can be run by a processor 310:

1. Let O be the roll orientation measured at time t

2. Calculate $S_t = \sum_{i=-N}^{0} O_{t+i} \times \dfrac{e^{\frac{(t+i-N)^2}{2R^2}}}{\sum_{x=0}^{N} e^{\frac{(x-N)^2}{2R^2}}}$ (smoothed orientation)

3. Calculate $r_t = S_t - S_{t-N}$ (derivative = roll velocity)

In the exemplary algorithm, N is the Gaussian-weighted window size, R is the Gaussian standard deviation, S is the smoothed orientation at time t and r is the derivative of the smoothed orientation. Such an algorithm can smooth the raw data and it can compute the instantaneous derivative.

Note that when a sensor records orientation data, the orientation range is from −180° to +180°. If the data go past +180°, the result will suddenly change to −180°, and vice versa. This effect has been termed a bound problem herein. Because of this potential bound problem, the signal may be discontinuous. In order to smooth the data signal, this discontinuous signal can be transformed to a continuous signal. Any common approach as is known in the art can be used to solve any bound problem. For instance, as a person cannot rotate his or her hand 180° in a very short time (less than 0.1 seconds), a simple and effective way to handle a bound problem is via the following algorithm:

```
if (R_t − R_(t−1) > 180)
  new_R_t = R_t − 360;
else if (R_t − R_(t−1) < −180)
  new_R_t = R_t + 360;
else
  new_R_t = R_t;
``` where R_t is the roll data at time t and R_(t−1) is the roll data at time t−1.

Smoothing can be done using a Gaussian-weighted window. The midpoint of the window corresponding to the peak of the Gaussian is centered on the current measurement, so that only a half of a Gaussian distribution is used for smoothing. The derivative can be computed simply as the difference between consecutive smoothed measurements. In order to implement this algorithm, the processor can buffer the most recent N measurements. The contents of the buffer can be updated after each new measurement, shifting out the previously stored oldest measurement. The value R denotes the width of the Gaussian relative to the buffer size used to smooth the data. The sensors of FIG. 6 are capable of sampling at 60 Hz. For data sampled at that rate, it has been found that having a buffer size of 2 seconds (N=120) with a Gaussian sigma defined by R=20 can produce good results. Of course, other parameters can alternatively be utilized, according to known methodology. For example, the sampling rate can be reduced to as low as about 15 Hz and corresponding algorithm parameters utilized and disclosed devices can be capable of detecting individual bites during a meal.

Additional manipulation of the data can be carried out to improve recognition of a single bite. For instance, individuals may wear a sensor at a different angle from one another. Under these circumstances, and using the absolute value of the roll, it may be difficult to define a bite period for a user. Accordingly, in one embodiment, the derivative of the smoothed roll data can be computed. Using the derivative data, the behavior of rotation can be comparable when the device is worn on the wrist at different angles. The derivative can be computed simply as the difference between consecutive smoothed measurements, i.e.:

$$d_t = s_t - s_{(t-Q)}$$

To calculate the derivative data, the above equation can be used in which $d_t$ is the derivative data and $s_t$ is the smoothed data at time t. For example, in one embodiment, the default value of Q (the derivative window size) can be 120 and the data collection frequency can be 60 Hz. Thus, the value for dt/2 will be the roll velocity (degrees/second).

In order to smooth the original roll data and compute the derivative of the smoothed roll data, the computer can buffer the most recent Q measurements. Moreover, the contents of the buffer can be updated after each new measurement, shifting out the previously stored oldest measurement.

Referring again to FIG. 7, it can be seen that the data recorded by the MEMS sensor 12 was much noisier than the data recorded by the InertiaCube 10. However, after applying the above described algorithm for smoothing and calculating the roll velocity from the raw data, the resulting signal is almost the same as is illustrated in the second column of the table of FIG. 7. Thus, a small sensor, such as a MEMS-based sensor, can be utilized in disclosed devices.

It should be understood that raw input data to processor 310 may be reduced to relevant emission peaks based on maximum variations between the peaks in the input data according to any data manipulation technique as would be understood by one of skill in the art. For instance, raw data can be processed according to a DAT method, or filtered by use of a method of interpolation or other methods such as a Kalman filter or by use of Gaussian distribution. Whether using raw or manipulated data, and based upon the threshold levels determined during calibration, the data can be differentiated to determine individual bites, specific examples of which are further described below.

Upon determination of the wrist roll velocity, either through direct measurement or manipulation of measured data, the information can be further manipulated to recognize and differentiate individual bites during a meal. One example of an algorithm for implementing the detection of a bite via the disclosed characteristic wrist roll is as follows:

1. Let START_BITE = 0
2. Let $V_t$ be the measured roll velocity at time t
3. If $V_t > T_1$ and START BITE = 0 then
   a. START_BITE = 1
   b. Let s = t
4. If $V_t < T_2$ and t−s > $T_3$ then
   a. Bite detected
   b. START_BITE = 0
5. Goto 2

The variable START_BITE notes the first event of the cycle of roll motion. The thresholds $T_1$ and $T_2$ are input parameters that define the roll velocities that will be exceeded to trigger detection of the first and second events of the roll motion (e.g., +10 and −10, respectively). The threshold $T_3$ defines the interval of time that can elapse between the first and second events of the roll motion (e.g., 2 seconds).

The input parameters can be preset according to a statistical average over a population, or can be individualized for a specific user. For instance, a device can be calibrated for a particular user upon initial purchase, at which time visual measurements can be taken of an individual user's typical eating habits, in order to identify the positive and negative roll velocities and typical eating speed that can be used to trigger the detection of an individual bite.

Moreover, a periodic automatic calibration period, as described above, can be used to set the input parameters for a device. For instance, $T_1$ can generally be between about +5 deg/sec and about +15 deg/sec; $T_2$ can generally be between about −5 deg/sec and about −15 deg/sec; and $T_3$ can generally be between about 1 sec and about 4 sec.

Figure 8:
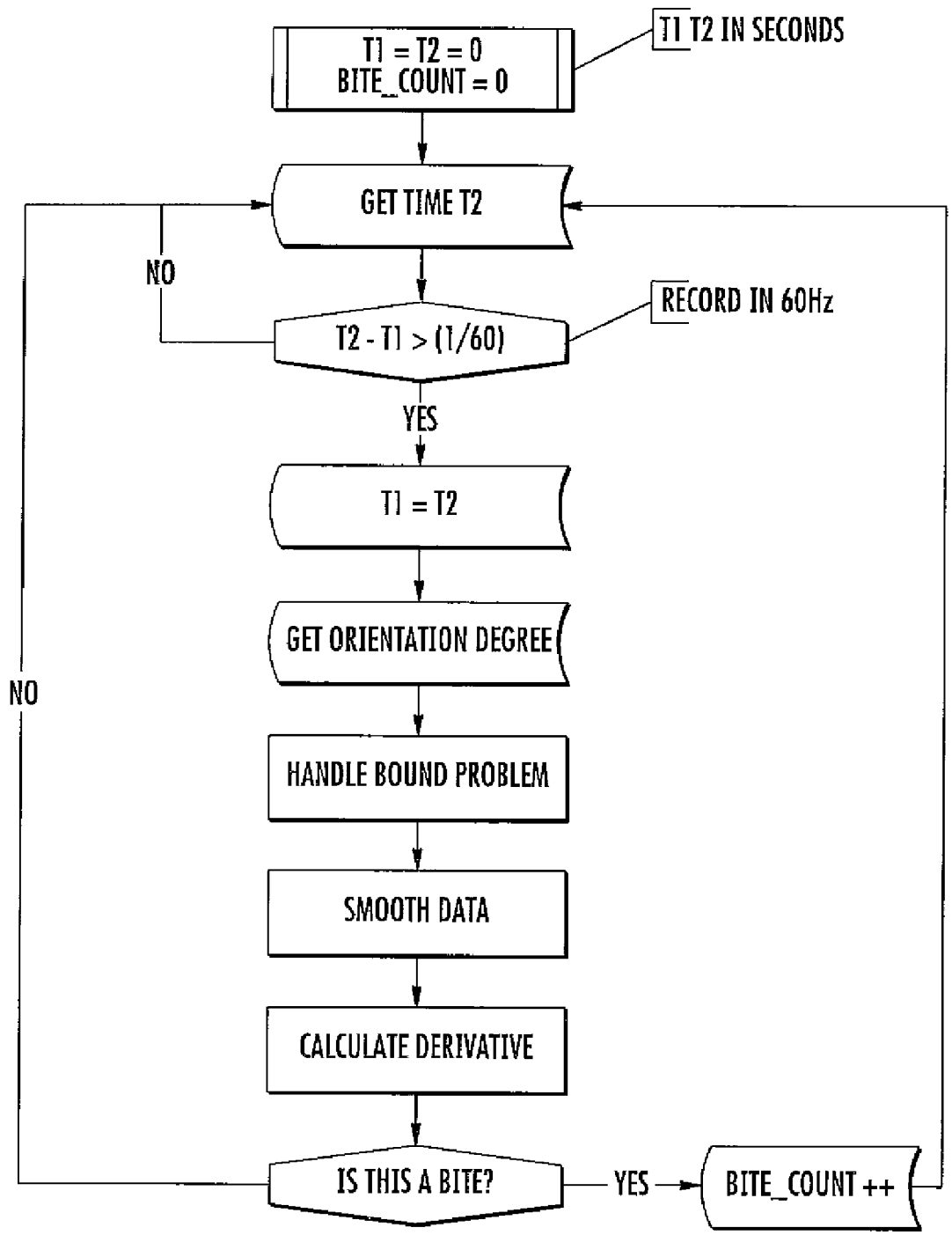
FIG. 8 illustrates a flow diagram for one embodiment of a bite detection algorithm as may be utilized in disclosed devices.

FIG. 8 illustrates a flow diagram of the above described bite detection algorithm. Before the loop, Bite Count in initialized as 0 as are two time parameters, T1 and T2. T1 is the previous time and T2 is the current time. When the time is updated by the system, if the current time is more than 1/60 of a second plus the old time, the old time is replaced with the current time and one sensor orientation datum is obtained from the sensor. Following, any bound problem is handled, the data is smoothed, the derivative is calculated, and a decision is made as to whether or not a bite has occurred at this time. If so, the parameter Bite Count will increase by 1 and the current time will be again obtained. If no bite is detected, the current time is obtained and the process repeats.

When software is used, any suitable programming, scripting, or other type of language or combinations of languages can be used to implement the teachings contained herein. However, software need not be used exclusively, or at all. For example, some embodiments of the methods and systems set forth herein can also be implemented by hard-wired logic or other circuitry, including, but not limited to application-specific circuits. Of course, combinations of computer-executed software and hard-wired logic or other circuitry can be suitable, as well.

The results of interpretation of the data of FIG. 7 according to the algorithm described above are illustrated on FIG. 7. Specifically, square 25 on FIG. 7 indicates those times at which $T_1$, the positive roll velocity threshold, was passed, mark 22 indicates those times at which $T_2$, the negative roll velocity threshold, was passed, and the marks 20 indicate the taking of a bite by the individual wearing the sensors.

Referring again to FIG. 5C, measurements made during each meal (e.g., total number of bites, average time between each bite, etc.) can be stored in non-volatile memory 312 that may correspond to a portion of microprocessor 310 or may be provided as a separate internal memory located within the device 100, or an external memory. In either case, the memory 312 can be sized to provide adequate data storage for a preselected time frame based on the number and types of measurements to be taken. In an exemplary embodiment of the device 100 the memory 312 is selected to provide sufficient storage to store at least 7 days of meals and may correspond to a memory capacity about 16 Kbytes, and smaller or larger memory capacity could be utilized in various embodiments.

In another embodiment, a memory can be sized to store data over a long period, for instance over several weeks or months, so as to provide very long term data to a user with regard to number of bites taken per meal/per day/per week, and so forth. Such long term data can provide objective feedback to a user as to the correlation between the number of bites of food a person takes and their ability to reach their target weight.

A set point as to number of bites can likewise be stored in memory 312. When the number of bites taken during a meal or over the course of a preset time period exceeds this set point, feedback can be provided to a user. Feedback can include one or more of a variety of effects. For example, physical feedback can be provided by an audible sound (e.g., buzzing), a tactile feedback (vibrating), a visual feedback (blinking), or any combination thereof. Feedback can be given for a variety of reasons, such as passing a user-specified threshold for a number of detected bites. The device can provide feedback based upon instantaneous or average time between bites. The device can provide feedback based upon an acceleration or deceleration of time between bites. The device can provide increasingly apparent feedbacks based upon an increasing number of bites detected. The device can provide feedback based upon total time spent eating. Any method that allows for the user to be alerted is encompassed in the present disclosure. Additional signaling can be utilized as well. For instance, if the user continues to take additional bites following the initial alert, device 100 may vibrate for a longer period of time or with increasing vibrational frequency. Optionally, the device could utilize a different method to re-notify the user such as the use of a discreet sound or the use of an electrical shock or any combination of vibrations, discreet sounds, electrical shocks, and so forth.

At the end of the meal, data recorded during the meal including, for instance, total number of bites, average time between bites, total time of meal, time of day of the meal, etc. can be stored in memory 312 and integrated into a long term informational data base.

With further reference to FIG. 5C, device 100 can include additional features. For instance, device 100 can include a Radio-frequency Identification ("RFID") chip 360 or other non-invasive and contactless user identification system that uniquely identifies the user. Device 100 may also include a contactless smart chip 370 (CSC) or other central processing unit with associated memory and integrated bus that enables the device 100 to perform bi-directional data communication with properly equipped external devices and systems. Additionally, device 100 may be battery operated by way of battery 380. Battery 380 may be a rechargeable battery and may be recharged by way of a separate battery charger device (not shown) including a built-in solar cell charging arrangement mounted on device 100.

External devices and systems with which device 100 can communicate can correspond to computer connectivity ports or devices such as a USB (or other data transfer type) computer connection that allow the exchange of user data from a device 100 to an external device. When user data has been exchanged from a device 100, the non-volatile memory 312 may be flushed and data acquisition in the device 100 begun again.

Data from device 100 may be transferred to an external device, e.g., a computer, via any communication link that may correspond to telephone modem, direct, wireless, and Internet connection or other communications methodologies as may be available or made available. Transmission of a signal to a remote site may be carried out with a radio frequency transmission scheme or with any other wireless-type transmission scheme, as is generally known in the art. For instance, a wireless telephone or internet communications scheme can be utilized to transmit a signal to a remote location according to known methods.

Wireless transmission systems as may be utilized in conjunction with disclosed devices and methods may include, for example, components and systems as disclosed in U.S. Pat. Nos. 6,289,238 to Besson, et al., 6,441,747 to Khair, et al., 6,802,811 to Slepian, 6,659,947 to Carter, et al., and 7,294,105 to Islam, all of which are incorporated in their entirety by reference.

An external device may be accessible to only the user of device 100 or may be a shared device. For instance, an external device may be a private computer, within the wearer's home, office, or so forth, or may be at a monitoring facility, for instance at a medical facility, such that appropriate medical personal may informed of the user's eating habits. Upon receipt of data from device 100 at the external device, the data may be converted to sequential user records and stored in a relational database format (RDBMS) where at least a User ID, Mode, and Date/Time of Measurement may be used as primary keys along with the User's unique ID (e.g., as maintained in the RFID chip 360).

In alternative embodiments, data obtained by device 100 may be transmitted to multiple receivers, so as to inform both the user and others (e.g., medical personnel) of the user's eating habits over a single meal, or over a long or short course of time.

A device as described herein can include additional sensors as well, in order to detect information about a user in addition to bite detection. For instance, a device can include a sensor array on a surface of a device that may correspond to a number of individual sensors that provide, in cooperation with additional control circuitry, for the automatic and periodic measurements of physiological and biometric properties including, without limitation, heart rate, blood pressure (systolic and diastolic), and other such physiological and biometric measurements as may be deemed desirable. For example, an additional sensor may be provided on a device that may correspond to an infrared sensitive diode that may be used to detect blood flow from which may be calculated both pulse rate and blood pressure.

According to another embodiment, a device as disclosed herein may incorporate a temperature sensor for detection the body temperature of a user, a moisture sensitive sensor that may provide information relative to body moisture loss, and so forth. Alternative choices of sensors as well as additional (or fewer) sensors may be selected as desired or necessary to provide data input to the device 100 as necessary for its particular design.

The disclosed device and method may be better understood with reference to the examples, set forth below.

EXAMPLE 1

Figure 9:
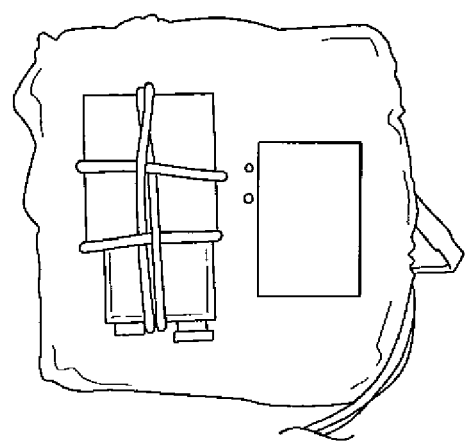
FIG. 9 illustrates one embodiment of a device as disclosed herein.

A device as illustrated in FIG. 9 was created, including wrist-worn strap that is a common wristband of the variety that is typically worn for exercise. The sensor utlilized was an InertiaCube 3 sensor produced by InterSense Corporation (Bedford, Mass.). The wired InertiaCube3 sensor is an inertial 3-DOF (Degree of Freedom) orientation tracking system. It is based on micro-electro-mechanical systems (MEMS) technology. It contains an accelerometer, a gyroscope and a magnetometer on each of the 3 axis so it can provide 360 degree measurement in all three orientations: pitch, yaw and roll. The whole sensor package includes the orientation sensor, the RS-232 serial interface, the AC power cable and the AC/DC +6VDC power supply.

The sensor was in communication with a desktop computer for digitizing and processing the data obtained from the sensor. The computer contained an A/D card, model PCI-DAS08 produced by Measurement Computing Corporation (Norton, Mass.). The sensor was mounted on the wrist strap such that the roll-axis of the sensor was parallel to the roll axis defined in FIGS. 1 and 2.

FIG. 10 provides images demonstrating the events defining the roll motion corresponding to a bite. In FIG. 10A, the subject's wrist has exceeded the threshold for positive roll; and in FIG. 10C, the subject's wrist has exceeded the threshold for negative roll; FIG. 10B shows the bite of food taken in between.

Figure 10A:
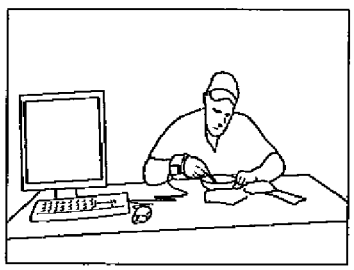
FIG. 10A-10C provide images of a single subject over the course of a single bite.
Figure 10B:
Figure 10C:
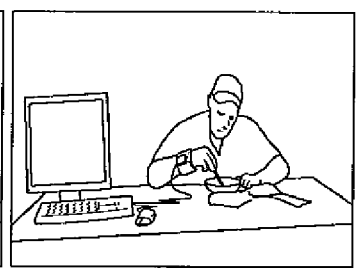
Figure 10D:
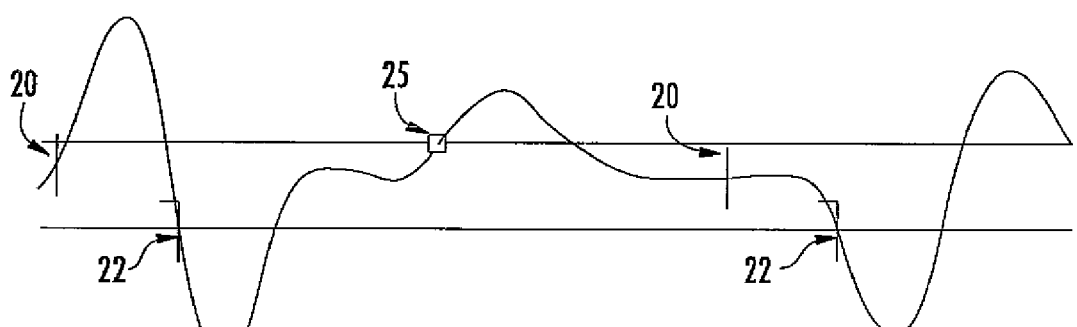
FIG. 10D illustrates the corresponding wrist roll data recorded simultaneously with the recording of the images of FIGS. 10A-10C by use of a sensor as illustrated in FIG. 9.

FIG. 10D illustrates the wrist roll data that was recorded simultaneously to the images shown in FIGS. 10A-10C. Square 25 marks when the positive roll velocity threshold was first exceeded, and corresponds to the image of FIG. 10A. The subsequent line 22 shows when the negative roll velocity threshold was first exceeded, and corresponds to the image of FIG. 10C. The line 20 corresponds to when the subject first placed food into his mouth, as shown in FIG. 10B.

EXAMPLE 2

Ten subjects were recorded eating a meal of their choice. A device as described above in Example 1 was placed on each subject's wrist and connected to an external computer. The computer recorded the raw sensor data and utilized algorithms as described herein to calculate the times at which bites were detected. The raw sensor data and bite detection times were correlated with a recorded video in order to evaluate the performance of the device. An evaluation program was written that allows the user to manually mark the times bites are actually taken, as well as review the motion events that disclosed methods used to detect bites.

For each subject, the number of bites taken during a meal was measured. This number varied from 19 to 65. Table 1, below, shows the number of bites taken by each subject, and the relationships between bites taken and wrist roll cycles. For 82% of the total bites, exactly one bite occurred between a positive roll and a subsequent positive roll (a wrist roll cycle).

TABLE 1

| Subject | Total bites taken | Bites occurring 1:1 with wrist roll cycle | Occurrences of >1 bite in a wrist roll cycle | Occurrences of 0 bites in a wrist roll cycle |
|---------|------|-----|----|----|
| 1  | 65 | 44 | 10 | 12 |
| 2  | 21 | 20 | 0  | 8  |
| 3  | 60 | 43 | 6  | 13 |
| 4  | 35 | 35 | 0  | 12 |
| 5  | 37 | 37 | 0  | 15 |
| 6  | 26 | 14 | 6  | 6  |
| 7  | 23 | 23 | 0  | 22 |
| 8  | 30 | 25 | 2  | 20 |
| 9  | 19 | 19 | 0  | 1  |
| 10 | 31 | 23 | 4  | 12 |

Table 2 provides the statistics for the bites taken that corresponded directly to wrist roll cycles (the bites in column 3 of Table 1). As can be seen, there is a great deal of variance on the time elapsed between the detected positive and negative roll motion events. This illustrates the benefit of detecting both events to verify a bite has been taken. This also provides evidence that bite detection through analysis of time intervals alone will not be particularly accurate. In addition, the last two columns of Table 2 show that in most cases the actual bite of food is taken between the positive and negative roll motion events.

TABLE 2

| Person | Average (variance) of time between +/− roll | Average (variance) of time between −/+ roll | Number of times bite is taken between +/− | Number of times bite is taken between −/+ |
|---|---|---|---|---|
| 1 | 8.0 (57.3) | 3.1 (4.8) | 40 | 14 |
| 2 | 8.7 (63.2) | 5.8 (31.8) | 14 | 6 |
| 3 | 7.9 (85.0) | 4.9 (18.0) | 44 | 5 |
| 4 | 4.3 (19.1) | 8.5 (28.7) | 31 | 4 |
| 5 | 6.3 (16.0) | 4.3 (8.5) | 35 | 2 |
| 6 | 9.6 (58.4) | 3.7 (13.2) | 17 | 3 |
| 7 | 7.0 (64.5) | 8.8 (61.7) | 19 | 4 |
| 8 | 4.0 (25.9) | 9.0 (96.5) | 21 | 6 |
| 9 | 6.2 (10.6) | 3.9 (2.7) | 19 | 0 |
| 10 | 6.7 (161.4) | 8.0 (237.2) | 18 | 9 |

Figure 11:
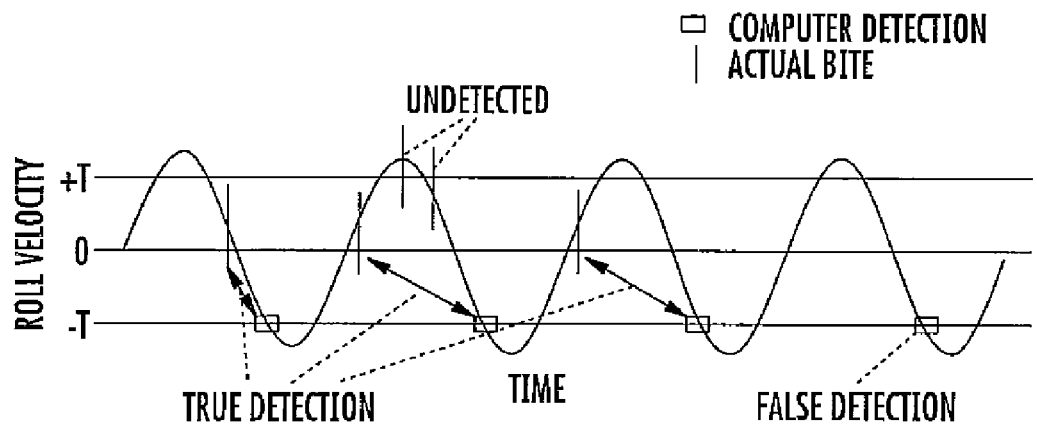
FIG. 11 illustrates the correspondence between bites detected by a device as disclosed herein and manually detected bites taken as evaluated during experimental runs.

To evaluate the performance of a bite detector, the correspondence of computer-detected wrist motion cycles to manually marked bites taken was calculated. FIG. 11 illustrates how detections were classified. For each wrist motion cycle detected, a single bite taken within its cycle was classified as a true detection. Any additional bites taken within that cycle were classified as undetected bites. A wrist motion cycle detected in which no bites occurred was classified as a false detection.

Table 3, below, summarizes the performance of the device using these classifications on each of the 10 subjects. Of all wrist roll cycles detected, 66% corresponded to actual bites, and 26% were false positives. The false positives were most often due to the use of a napkin to wipe the mouth, or to stirring or manipulating food in a manner that did not result in a bite. Only 7.7% of actual bites went undetected. Thus, the device errs on the side of over-detection. Such a bias can be incorporated into statistical calculations used to track the total number of bites eaten during a meal, feedback can be modified accordingly.

TABLE 3

| Person | True detections | False detections | Undetected | Sensitivity |
|---|---|---|---|---|
| 1 | 54 | 12 | 11 | 83% |
| 2 | 20 | 8 | 1 | 95% |
| 3 | 49 | 13 | 11 | 82% |
| 4 | 35 | 12 | 0 | 100% |
| 5 | 37 | 15 | 0 | 100% |
| 6 | 20 | 6 | 6 | 77% |
| 7 | 23 | 22 | 0 | 100% |
| 8 | 27 | 20 | 3 | 90% |
| 9 | 19 | 1 | 0 | 100% |
| 10 | 27 | 12 | 4 | 87% |
| Average | 66% | 26% | 7.7% | 91% |

Although the chosen default parameter setting and sample rate worked quite well in this example, these default settings are based on selection, and there may exist other good parameters. Importantly, this exemplified embodiment of a bite detector device is a sensor of small size which is wearable.

If one were to down-sample and change some default parameters, fewer buffers can be used in the memory, which can both increase the speed of the algorithm and decrease the size of the memory on the device. The default values used in this example were the following:

1. Sample rate is 60 Hz.
2. Gaussian-weighted window size N=120.
3. Gaussian standard deviation R=20.
4. Derivative window size Q=120.
5. Roll velocities that must be exceeded to trigger detection of the first events of the roll motion—T1=10 degrees/second.
6. Roll velocities that must be exceeded to trigger detection of the second events of the roll—T2=−10 degrees/second.
7. Interval of time that must elapse between the first and second events of the roll motion is T3=2 seconds.

Table 4 shows the comparison between down-sampling and the default 60 Hz data recording rate. Some other parameters settings were also changed. Specifically, when the system was run at a down-sample of 10 Hz, default parameters were as follows: N=20, R=3, Q=20, T1=10, T2=−10, and T3=2 seconds. The data in the parentheses is the result sampled at 60 Hz. There are a total 304 of true detections when sampled at 10 Hz, and 311 true detections when sampled at 60 Hz; there are a total 128 of false detections when sampled at 10 Hz, and 121 false detections when sampled at 60 Hz; there are a total 43 of undetected bites when sampled at 10 Hz, and 36 undetected bites when sampled at 60 Hz. When sampled at 10 Hz, there are only seven less true detections, seven more false detections and seven more undetected bites. Thus, if one were to be bounded by limited memory and limited processing in a device, down-sampling and use of fewer buffers is an alternative method that could still perform relatively well.

TABLE 4

| Person | True Detections | False Detections | Undetected |
|---|---|---|---|
| 1 | 54 (54) | 10 (12) | 11 (11) |
| 2 | 20 (20) | 9 (8) | 1 (1) |
| 3 | 50 (49) | 13 (13) | 10 (11) |
| 4 | 35 (35) | 13 (12) | 0 (0) |
| 5 | 36 (37) | 15 (15) | 1 (0) |
| 6 | 21 (20) | 7 (6) | 5 (6) |
| 7 | 22 (23) | 22 (22) | 1 (0) |
| 8 | 23 (27) | 24 (20) | 7 (3) |
| 9 | 19 (19) | 0 (1) | 0 (0) |
| 10 | 24 (27) | 15 (12) | 7 (4) |
| Total | 304 (311) | 128 (121) | 43 (36) |

EXAMPLE 3

Participants (N=21) ate a meal in a laboratory setting, and the sensitivity and positive predictive value (PPV) of a bite detector as described above in Example 1 were calculated. Parameters were set as described above in Example 2, i.e.:

1. Sample rate is 60 Hz.
2. Gaussian-weighted window size N=120.
3. Gaussian standard deviation R=20.
4. Derivative window size Q=120.
5. Roll velocities that must be exceeded to trigger detection of the first events of the roll motion is T1=10.
6. Roll velocities that must be exceeded to trigger detection of the second events of the roll
7. Interval of time that must elapse between the first and second events of the roll motion is T3=2 seconds.

A video camera recorded the meal. It was positioned to record when the participant took a bite of food. This enabled the experimenter to review the video and determine if the bite detector correctly detected, falsely detected, or missed bites. The video camera was positioned to the side of the participant to minimize the participant's awareness of the video camera.

The sensitivity of the bite detector was calculated for each participant in order to describe the proportion of bites that were correctly identified by the bite detector. True-positives (TPs) were defined as the participant taking a bite and a bite being detected. False-negatives (FNs) were defined as taking a bite and a bite not being detected. Sensitivity was calculated as TP/(TP+FN) and converted into a percentage. The positive predictive value (PPV) was calculated for each participant in order to determine the probability that the bite detector would correctly detect a bite. False positives (FPs) were defined as the participant not taking a bite and a bite being detected. PPV was calculated as TP/(TP+FP) and converted into a percentage. Table 5, below, shows the sensitivity and PPV for each participant.

TABLE 5

| Participant Number | TP | FP | FN | Sensitivity | PPV (%) |
|---|---|---|---|---|---|
| 1 | 68 | 12 | 0 | 100 | 85 |
| 2 | 20 | 11 | 0 | 100 | 65 |
| 3 | 19 | 2 | 0 | 100 | 90 |
| 4 | 27 | 7 | 0 | 100 | 79 |
| 5 | 32 | 3 | 0 | 100 | 91 |
| 6 | 26 | 5 | 0 | 100 | 84 |
| 7 | 46 | 11 | 0 | 100 | 81 |
| 8 | 49 | 8 | 2 | 96 | 86 |
| 9 | 34 | 8 | 2 | 94 | 81 |
| 10 | 28 | 9 | 0 | 100 | 76 |
| 11 | 49 | 1 | 0 | 100 | 98 |
| 12 | 48 | 4 | 0 | 100 | 92 |
| 13 | 59 | 13 | 0 | 100 | 82 |
| 14 | 27 | 10 | 0 | 100 | 73 |
| 15 | 17 | 7 | 0 | 100 | 71 |
| 16 | 30 | 5 | 1 | 97 | 86 |
| 17 | 20 | 7 | 3 | 87 | 74 |
| 18 | 23 | 6 | 1 | 96 | 79 |
| 19 | 27 | 9 | 0 | 100 | 75 |
| 20 | 10 | 13 | 1 | 91 | 43 |
| 21 | 9 | 4 | 2 | 82 | 69 |

EXAMPLE 4

A second detector was formed including a wireless InertiaCube3 sensor which is produced by the InterSense Corporation (InterSense, Inc., 36 Crosby Drive, Suite 150, Bedford, Mass. 01730). The wireless InertiaCube3 sensor is an inertial 3-DOF (Degree of Freedom) orientation tracking system similar to the wired InertiaCube3 sensor utilized in the above examples. The main difference between these two sensors is that the wireless InertiaCube3 sensor can connect to the computer wirelessly and it allows up to 16 different channel selections. It consists of a wireless InertiaCube3 sensor and an InertiaCube3 receiver which uses the same channel.

To get the orientation data from the wireless InertiaCube3 sensor, a 9 volt battery was attached to the wireless InertiaCube3 sensor and the receiver was connected to the computer through a USB port.

The software "DeviceTool" provided by the InterSense company was used to configure the wireless InertiaCube3 sensor and the InertiaCube3 receiver. The software searches for all linked receivers and the paired wireless InertiaCube3 sensor. The same library ISENSE.DLL and the same functions as the wired InertiaCube3 sensor described above can be used to read the orientation data from the sensor wirelessly.

EXAMPLE 5

The third prototype uses a MEMS inertial sensor LIS3L02AL produced by STMicroelectronics Corporation (STMicroelectronics, 39 Chemin du Champ des Filles, C.P.21, CH 1228 Plan-Les-Ouates, Geneva, Switzerland, www.st.com). The sensor 12 is shown in FIG. 6.

The LIS3L02AL is a 3-axis linear capacitive accelerometer. It is small, has low power consumption and has a bandwidth of 1.5 KHz.

Figure 12:
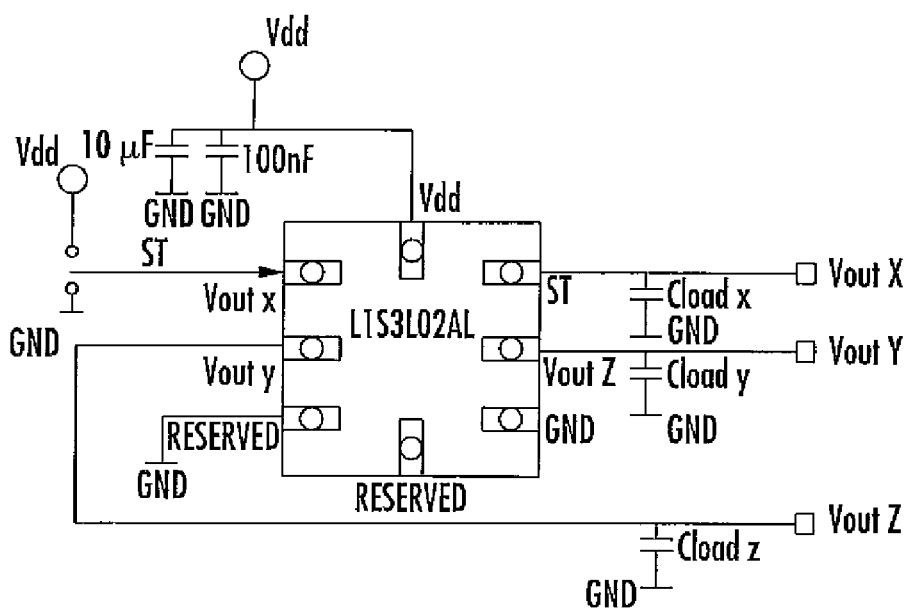
FIG. 12 illustrates a circuit design for a sensor utilized in a device as described herein.

FIG. 12 shows the circuit design for a STMicroelectronics LIS3L02AL sensor that was designed and utilized in forming a device.

A power supply decoupling capacitor (100 μF ceramic or polyester +10 μF aluminum) was connected to the Vdd leg of the device. The LIS3L02AL allows to band limit Voutx, Vouty and Voutz through the use of external capacitors. The frequency range was less than 1.5 KHz. The equation for the cut-off frequency (ft) of the external filter is:

$$f_t = \frac{1}{2\pi \cdot R_{out} \cdot C_{load}(x, y, z)}$$

$R_{out}$ has a nominal value equal to 110 kΩ, so this Equation can be simplified to:

$$f_t = \frac{1.45 \mu F}{C_{load}(x, y, z)} [Hz]$$

In this design, a 22 nF capacity was chosen as $C_{load}(x)$, $C_{load}(y)$, and $C_{load}(z)$, thus calculating from the above equation, the cut-off frequency of the external filter was 66 Hz.

A test mode of the circuit was also built. In FIG. 12, when the wire from ST was connected to Vdd, the circuit was in test mode; otherwise the circuit was in normal mode.

Figure 13:
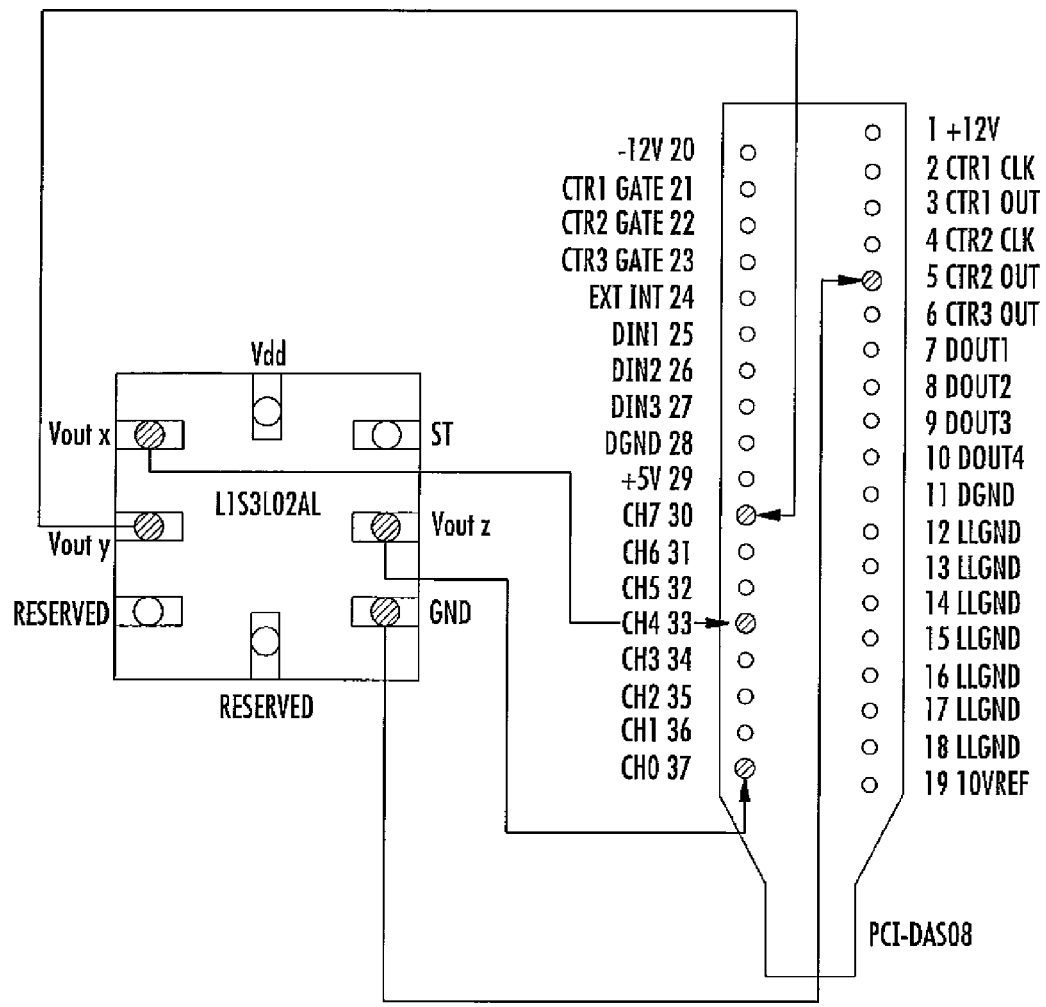
FIG. 13 illustrate the main connector pinout of an analog input-to-digital I/O board and the connection with a sensor as described herein.

The LIS3L02AL sensor was attached to an analog input-to-digital I/O board in a computer. The PCI-DAS08 produced by Measurement Computing Corporation (Measurement Computing Corporation, 10 Commerce Way, Norton, Mass. 02766, USA) was used. The PCI-DAS08 is a multifunction measurement and control board designed to operate in computers with PCI bus accessory slots. All hardware configuration options on the PCI-DAS08 are software controlled. There are no switches or jumpers to set. The board uses a 37-pin male "D" connector. The main connector pinout of the analog input-to-digital 110 PCI-DAS08 board and the connection with the STMicroelectronics LIS3L02AL sensor are shown in FIG. 13.

It will be appreciated that the foregoing examples, given for purposes of illustration, are not to be construed as limiting the scope of this disclosure. Although only a few exemplary embodiments of the disclosed subject matter have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. A device for determining that a bite of food has been taken by a subject, the device comprising:
   a sensor that monitors a positive roll velocity and a negative roll velocity of a hand, arm, wrist, or any combination thereof of a subject; and
   an electronic processor for receiving raw data concerning the positive roll velocity and the negative roll velocity of the hand, arm, wrist, or any combination thereof of the subject from the sensor, the electronic processor carrying out data manipulation to form processed data, the processed data including determination that the positive roll velocity exceeds a threshold positive roll velocity and the negative roll velocity exceeds a threshold negative roll velocity and that a pause of between about 0.5 seconds and about 10 seconds exists between the positive roll velocity and the negative roll velocity to determine that a bite of food has been taken by the subject.

2. The device of claim 1, further comprising an electronic memory for storing the processed data.

3. The device of claim 2, wherein the electronic memory further stores a number of bites taken by a user during a meal or over a period of time.

4. The device of claim 1, further comprising a user interface for providing to the subject information concerning the determination of a bite of food taken by the subject.

5. The device of claim 1, further comprising an attachment device for attaching the sensor to the clothing or body of the subject.

6. The device of claim 5, wherein the attachment device comprises a wrist band or an adhesive.

7. The device claim 1, wherein the sensor is a multi-axis accelerometer, a gyroscope, a MARG sensor, or a magnetometer.

8. The device of claim 1, further comprising one or more additional sensors.

9. The device of claim 8, the one or more additional sensors including a sensor for monitoring at least one of the pitch and yaw motion of the hand, arm, wrist, or any combination thereof of the subject; for monitoring a physiological property of the subject; or for monitoring the time taken between individual bites.

10. The device of claim 1, further comprising a housing that encloses the sensor.

11. The device of claim 1, wherein the sensor is in wireless communication with the electronic processor.

12. The device of claim 1, further comprising a communications link for transferring data from the device to an external device.

13. The device of claim 1, further comprising a power source.

14. A device for determining that a bite of food has been taken by a subject, the device comprising:
   a sensor that monitors at least a positive roll motion and a negative roll motion of a hand, arm, wrist, or any combination thereof of a subject; and
   an electronic processor for receiving raw data concerning at least the positive roll motion and the negative roll motion of the hand, arm, wrist, or any combination thereof of the subject from the sensor, the electronic processor carrying out data manipulation on the raw data to form processed data, the processed data including determination that a bite of food has been taken by the subject.

15. The device of claim 14, further comprising an electronic memory for storing the processed data.

16. The device of claim 15, wherein the electronic memory further stores a number of bites taken by a user during a meal or over a period of time.

17. The device of claim 14, further comprising a user interface for providing to the subject information concerning the determination of a bite of food taken by the subject.

18. The device of claim 14, further comprising an attachment device for attaching the sensor to the clothing or body of the subject.

19. The device claim 14, wherein the sensor is a multi-axis accelerometer, a gyroscope, a MARG sensor, or a magnetometer.

20. The device of claim 14, wherein the sensor is in wireless communication with the electronic processor.

21. The device of claim 14, further comprising a communications link for transferring data from the device to an external device.

22. A method for determining that a bite of food has been taken by a subject, the method comprising:
   sensing raw data concerning positive roll velocity and negative roll velocity of a hand, arm, wrist, or any combination thereof of a subject;
   electronically processing the raw data with a processor to develop processed data, the processed data comprising a pattern of motion, the pattern of motion including
   (a) a positive roll of the hand, arm, wrist, or any combination thereof of a subject that is determined when the positive roll velocity exceeds a threshold positive roll velocity,
   (b) a negative roll of the hand, arm, wrist, or any combination thereof of a subject that is determined when the negative roll velocity exceeds a threshold negative roll velocity; and
   (c) a pause of between about 0.5 seconds and about 10 seconds between (a) and (b), wherein upon recognition by the processor of the pattern of motion, the processor registers that a bite of food has been taken by the subject.

23. The method according to claim 22, further comprising electronically storing the processed data in a memory.

24. The method according to claim 22, further comprising providing information concerning the processed data to the subject via a user interface.

25. The method according to claim 24, wherein the information concerning the processed data is provided to the subject via an auditory, tactile, or visual signal, or a combination thereof.

26. The method according to claim 22, further comprising sensing additional data.

27. The method according to claim 26, the additional data being raw data concerning at least one of the yaw motion and the pitch motion of the hand, arm, wrist, or any combination thereof of the subject, or a physiological property of the subject.

28. The method according to claim 22, wherein the threshold positive roll velocity is between about +5 degrees per second and about +15 degrees per second and the threshold negative roll velocity is between about −5 degrees per second and about −15 degrees per second.

29. The method according to claim 23, further comprising communicating information from the memory to an external device via a wired or wireless electronic communication methodology.

30. The method according to claim 22, wherein the step of electronically processing the raw data comprises smoothing the raw data to form smoothed data.

31. The method according to claim 30, wherein the step of electronically processing the raw data comprises determining the derivative of the smoothed data.

32. The method according to claim 22, further comprising storing information in an electronic memory with regard to at least one of a total number of bites taken by the subject over the course of a single meal, over the course of multiple meals, or over a period of time.

33. A method for determining that a bite of food has been taken by a subject, the method comprising:
   sensing raw data concerning a positive roll motion and a negative roll motion of a hand, arm, wrist, or any combination thereof of a subject;
   electronically processing the raw data with a processor to develop processed data, the processed data comprising a pattern of motion, the pattern of motion including
   (a) a positive roll of the hand, arm, wrist, or any combination thereof of a subject,
   (b) a negative roll of the hand, arm, wrist, or any combination thereof of a subject; and
   (c) a pause of between about 0.5 seconds and about 10 seconds between (a) and (b), wherein upon recognition by the processor of the pattern of motion, the processor registers that a bite of food has been taken by the subject.

34. The method according to claim 33, further comprising electronically storing the processed data in a memory.

35. The method according to claim 34, further comprising providing information concerning the processed data to the subject via a user interface.

36. The method according to claim 35, wherein the information concerning the processed data is provided to the subject via an auditory, tactile, or visual signal, or a combination thereof.

* * * * *

UNITED STATES PATENT AND TRADEMARK OFFICE
CERTIFICATE OF CORRECTION

PATENT NO. : 8,310,368 B2
APPLICATION NO. : 12/686656
DATED : November 13, 2012
INVENTOR(S) : Hoover et al.

It is certified that error appears in the above-identified patent and that said Letters Patent is hereby corrected as shown below:

In the specification

Column 1, between line 10 and "BACKGROUND", please enter the following:

-- FEDERALLY SPONSORED RESEARCH AND DEVELOPMENT

This invention was made with government support under grant #2R42DK091141-02, May 2014 and grant #1R41DK091141-01A1, August 2011 awarded by The National Institutes for Health. The government has certain rights in the invention. --

Signed and Sealed this
Nineteenth Day of April, 2016

Michelle K. Lee
*Director of the United States Patent and Trademark Office*